US006551469B1

(12) United States Patent
Nair et al.

(10) Patent No.: US 6,551,469 B1
(45) Date of Patent: Apr. 22, 2003

(54) PHOTOCHLORINATION OF 1,1,1,3,3-PENTAFLUOROPROPANE

(75) Inventors: Haridasan K. Nair, Williamsville, NY (US); Michael Van Der Puy, Amherst, NY (US); David Nalewajek, West Seneca, NY (US); Timothy R. Demmin, Grand Island, NY (US); Andrew J. Poss, Kenmore, NY (US); David E. Bradley, Buffalo, NY (US); Ian R. Shankland, Randolph, NJ (US); Martin E. Cheney, Buffalo, NY (US)

(73) Assignee: Honeywell International, Morristown, NJ (US)

( * ) Notice: Subject to any disclaimer, the term of this patent is extended or adjusted under 35 U.S.C. 154(b) by 0 days.

(21) Appl. No.: 09/994,438

(22) Filed: Nov. 27, 2001

(51) Int. Cl.⁷ ............................ C07C 17/00; C07C 17/10
(52) U.S. Cl. .................................. 204/157.95; 570/176
(58) Field of Search ....................... 570/176; 204/157.95

(56) References Cited

U.S. PATENT DOCUMENTS

| 4,060,469 A | 11/1977 | Sweeney et al. |
| 5,421,971 A | 6/1995 | Van Der Puy et al. |
| 5,710,352 A | 1/1998 | Tung |
| 5,728,904 A | 3/1998 | Van Der Puy et al. |
| 5,951,830 A | 9/1999 | Bertocchio et al. |
| 5,969,198 A | 10/1999 | Thenappan et al. |
| 6,023,004 A | 2/2000 | Thenappan et al. |
| 6,077,982 A | 6/2000 | Yates et al. |
| 6,187,976 B1 | 2/2001 | Van Der Puy et al. |

OTHER PUBLICATIONS

J. Chen et al., J. Phys. Chem. A, 1997, 101, 2648–2653, 2649.
Kirk–Othmer Encyclopedia of Chemical Technology, vol. 17, pp. 545–555 (3d ed. 1982).

Primary Examiner—Alan Siegel
(74) Attorney, Agent, or Firm—Collen D. Szuch; Deborah M. Chess

(57) ABSTRACT

A process for preparing 1-chloro-1,1,3,3,3-pentafluoropropane, $CF_3CH_2CF_2Cl$, comprising contacting in a reaction zone in the substantial absence of oxygen, reactants comprising chlorine and 1,1,1,3,3-pentafluoropropane, $CF_3CH_2CHF_2$ (also referred to as HFC-245fa), and subjecting the reactants to actinic radiation, such as UV light at about 2,000 to 4,000 Angstroms, wherein: (1) inert gas is present at a concentration equal to or less than about 5 wt. % of the total weight of reactants; (2) the molar ratio of chlorine to $CF_3CH_2CHF_2$ is from about 0.2:1 to about 1.5:1; and (3) the concentration of chlorinated product produced having greater than one chlorine present in the molecule is less than or equal to about 10 wt. %.

30 Claims, No Drawings

PHOTOCHLORINATION OF 1,1,1,3,3-PENTAFLUOROPROPANE

BACKGROUND OF THE INVENTION

This invention relates to a process for producing hydrochlorofluorocarbons (i.e., compounds that contain only hydrogen, fluorine, chlorine and carbon atoms, HCFCs) that are useful for producing fluorine-containing olefins, which are themselves useful as intermediates for making industrial chemicals, including polymers. HCFCs can also be used in place of chlorofluorocarbons, (i.e., compounds that contain only carbon, chlorine and fluorine atoms, CFCs) since the latter have been implicated in the depletion of stratospheric ozone and HCFCs are believed to contribute less to such depletion. More particularly, the present invention relates to a process for producing 1-chloro-1,1,3,3,3-pentafluoropropane or $CF_3CH_2CF_2Cl$ (also designated "HCFC-235fa"), by photochlorinating 1,1,1,3,3-pentafluoropropane, or $CF_3CH_2CHF_2$, (also designated "HFC-245fa").

U.S. Pat. No. 6,187,976 B1 describes the preparation of 1-chloro-1,1,3,3,3-pentafluoropropane by reacting, in the liquid or vapor phase, $CCl_3CH_2CCl_3$ with hydrogen fluoride in the presence of a fluorination catalyst.

The production of $CF_3CH_2CF_2Cl$ occurs as an intermediate during the production of $CF_3CH_2CHF_2$, as described in U.S. Pat. No. 5,728,904, incorporated herein by reference to the extent permitted. That method involves conversion of $CCl_3CH_2CCl_3$ to $CF_3CH_2CF_2Cl$ by reaction with HF in the presence of a fluorination catalyst, selected from $TiCl_4$, $SnCl_4$ or mixtures thereof.

The UV catalyzed reaction of $CF_3CH_2CHF_2$ and chlorine to produce $CF_3CH_2CF_2Cl$ is described by J. Chen et al., J. Phys. Chem. A, 1997, 101, 2648–2653, 2649. The reaction was carried out in the absence of oxygen and using a mixture of $CF_3CH_2CF_2H$ at a concentration range of 0.4–0.7 Torr and $Cl_2$ at a concentration range of 3–4 Torr; the overall system diluted in 700 Torr of helium. The corresponding molar ratio of chlorine to $CF_3CH_2CHF_2$ for this system ranged from 4.3 to 10:1. In this highly dilute, inert environment (at most, the reactants represented only 0.7% of the overall composition), it is said that the primary reaction products were $CF_3CH_2CF_2Cl$ and HCl. The conditions and process described, while suitable for academic research, are not amenable to scale-up and industrial use.

While the photochlorination of fluorine-containing hydrocarbons is described in the patent literature, it is in connection with the purification of 1,1,1,3,3-pentafluoropropane, HFC-245fa, by chlorinating olefinic impurities, U.S. Pat. Nos. 6,077,982 and 5,951,830; and the production of HCFCs (and HFCs), wherein the HCFC compounds contained more than one chlorine atom, U.S. Pat. Nos. 5,421,971 and 4,060,469. In particular, U.S. Pat. No. 6,077,982 discloses that the amount of chlorine added relative to the unsaturated impurity present can range from about 1 to 1.5 times the concentration of the unsaturated impurity (col. 3, lines 4–6) and the concentration of the unsaturated species is from about 300–20,000 wt. ppm (col. 2, lines 55–56). Based on these values, the maximum ratio of chlorine to HFC-245fa disclosed in this patent is about 0.1. While the patent discloses that increasing the amount of chlorine relative to the amount of impurity improves its chlorination and ultimate removal, the increase is within the scope of the range disclosed and there is no recognition that further increases run the risk of chlorinating or over-chlorinating the primary product, HFC-245fa. In fact, chlorination of HFC-245fa is contrary to the objectives of this patent.

There is a continuing need for the production of HFC-235fa, a useful industrial chemical, using a controlled process that produces little or no undesirable by-products.

SUMMARY OF THE INVENTION

A process for preparing 1-chloro-1,1,3,3,3-pentafluoropropane, $CF_3CH_2CF_2Cl$, comprising contacting in a reaction zone in the substantial absence of oxygen reactants comprising chlorine and 1,1,1,3,3-pentafluoropropane, $CF_3CH_2CHF_2$, and subjecting the reactants to actinic radiation, wherein: (A) inert gas is present at a concentration equal to or less than 5 wt. % of the total weight of said reactants; and (B) the concentration of chlorinated product produced having greater than one chlorine present in the molecule is less than or equal to about 10 wt. %.

DETAILED DESCRIPTION

As used herein, "actinic radiation" means light irradiation of sufficient intensity and at appropriate wavelengths, including ultraviolet and visible light, but preferably wavelengths shorter than those of visible light, such that the radiation causes photochemical effects, especially including chemical reaction between chlorine and 1,1,1,3,3-pentafluoropropane.

Various methods for producing 1,1,1,3,3-pentafluoropropane or HFC-245fa are described in U.S. Pat. Nos. 5,710,352; 5,969,198; and 6,023,004. Another method, described in U.S. Pat. No. 5,728,904, is said to be economical, amenable to large scale application and uses readily available raw materials. The process of that patent uses three steps, as follows: 1) formation of $CCl_3CH_2CCl_3$ by the reaction of $CCl_4$ with vinylidene chloride; 2) conversion of $CCl_3CH_2CCl_3$ to $CF_3CH_2CF_2Cl$ by reaction with HF in the presence of a fluorination catalyst, selected from $TiCl_4$, $SnCl_4$ or mixtures thereof; and 3) reduction of $CF_3CH_2CF_2Cl$ to $CF_3CH_2CF_2H$. The disclosures of each of these four patents are incorporated herein to the extent permitted. Commercial quantities of $CF_3CH_2CHF_2$, or HFC-245fa, also are available from Honeywell International Inc., Morristown, N.J. for use as a reactant in the present process.

The preferred reaction of the present process between HFC-245fa and chlorine in the presence of actinic radiation causes substitution of a covalently bonded hydrogen atom in the substrate molecule by chlorine, as represented by the following equation:

$$CF_3CH_2CHF_2 + Cl_2 \rightarrow CF_3CH_2CF_2Cl + HCl$$

Undesirable multichlorinated byproducts include, for example, 1,1,1,3,3-pentafluoro-2,2,3-trichloropropane, $CF_3CCl_2CF_2Cl$, and $CF_3CHClCF_2Cl$.

The apparatus used for photochlorination can be any suitable reactor capable of containing the reactants at the temperature and pressure during the photochlorination reaction and also containing an appropriate actinic radiation source or sufficiently transparent to actinic radiation in the desired wavelength range. For example, the reactor can be constructed of suitably corrosion-resistant metal, metal lined with glass or plastic, or glass, in other words a material suitably resistant to the corrosive effects of chlorine, and include a well, for example a quartz well, in which a light source is located. Alternatively, the reactor can be constructed of glass and the light source can be external to the reaction zone, but irradiating the reaction zone or focused thereon. Preferably, the reactor includes means to mix or stir reactants in the liquid and/or vapor phase and at least one condenser or cold trap in order to control the reactants and reaction products. The apparatus preferably includes at least one inlet for the reactants and at least one outlet for the reaction by-products. For example, multiple inlets are provided, one for HFC-245fa and one for chlorine. A suitable reactor consists of a glass reactor, of appropriate size for producing the quantities of product desired, equipped with a condenser or cold trap, a magnetic stirrer, and fitted with a water cooled, quartz immersion well for placement of a 450 watt, quartz, medium pressure, mercury vapor lamp, e.g., providing radiation at about 200–400 nm, and having an inlet for the introduction of chlorine and an outlet for gaseous products. Such an apparatus, having a capacity of 1 liter, is available from Ace Glass Co., Vineland, N.J. In addition, the *Kirk-Othmer Encyclopedia of Chemical Technology*, Vol. 17, pages 545–555 (3d ed. 1982) contains a general description of the types of light sources and reactors that may be used; this portion of the reference is incorporated herein to the extent permitted.

Desirably the reaction zone is maintained at a temperature of from about −5° C. to about +10° C.; preferably is maintained from about −3° C. to about +5° C.; more preferably from about −0° C. to about +2° C. Typically the reaction zone is maintained at a temperature such that HFC-245fa is present in both the liquid and vapor phase during the course of the reaction.

When it is introduced as a separate feed stream, chlorine is typically introduced into the reactor as a gas. The flow rate of the chlorine gas should be carefully regulated and controlled so that the molar ratio of chlorine relative to HFC-245fa in the reaction zone typically does not exceed about 1.5:1; preferably it does not exceed about 1.3:1; more preferably it does not exceed about 1.2:1; most preferably it does not exceed about 1.1:1. As for the minimum amount of chlorine required for the reaction, the ratio of chlorine to HFC-245fa is typically about 0.2:1; preferably about 0.3:1; more preferably, about 0.5:1; most preferably about 0.75:1; for example, about 0.9:1. Each of the expressed lower and upper concentrations can be combined to construct suitable ranges for the ratio of chlorine to HFC-245fa; for example, from about 0.2 to about 1.5; from about 0.2 to about 1.1; from about 0.5 to about 1.1; etc. The most preferred ratio is from about 1.0: to about 1.2:1. If the feed rate or amount of chlorine relative to the amount of HFC-245fa is too low, the process can be economically unattractive, e.g., the amount of chlorinated product produced is unacceptably low. Conversely, if the ratio of chlorine to HFC-245fa is too high, an excessive amount of by-products containing more than one chlorine on the hydrochlorofluorocarbon (a "multichlorinated" product) is obtained. For convenience, particularly when a batch or titration-type process is practiced (see below for a description of the latter), the molar ratio of chlorine to HFC-245fa can be calculated based on the total amount of each reactant used during the course of the process; in such event, the ratios expressed above should be maintained in order to achieve the benefits of the present invention.

Typically the product of the process will contain less than about 10 wt. % multichlorinated product; preferably less than about 6 wt. %; more preferably less than about 4 wt. %. It is particularly preferred that no such multichlorinated products be produced, but a trace level of multichlorinated product may be expected, for example from greater than about zero to less than about 1 wt. %; preferably less than about 0.5 wt. %; more preferably less than about 0.1 wt. %; still more preferably less than about 0.05 wt. %; for example from greater than zero to less than about 0.025 wt. %.

Chlorine can be fed to the reactor in several ways. It can be introduced to the reactor by way of a feed line and enter the reactor preferably by way of a sintered glass sparger, for example, submerged under liquid HFC-245fa already present in the reactor; it can be added to the vapor phase of the reactor; it can be premixed with HFC-245fa, for example, if the latter is to be fed continuously, at a distance upstream from the reactor in order to partially or thoroughly saturate the HFC-245fa before the mixture enters the reactor; it can be premixed with HFC-245fa as described and also be present in excess in the premixed stream. Preferably chlorine is fed to the reactor as a gas through a sparger under HFC-245fa that is present in the reactor as a liquid phase; and wherein chlorine and/or HFC-245fa can also be present in the vapor phase at the temperature and pressure conditions of the reactor. In this manner the chlorine can be introduced for a period of time so as to partially or fully saturate the HFC-245fa liquid prior to initiating the photo-chlorination reaction by providing actinic radiation.

The process of the present invention can be carried out as a batch reaction, a semi-continuous reaction or as a continuous reaction. By a semi-continuous reaction is meant where effectively all of the HFC-245fa is fed to the reaction zone and thereafter chlorine gas is introduced into the reactor, preferably sparged into the HFC-245fa at a controlled rate. During the course of the reaction chlorine gas is introduced in a controlled manner to maintain the ratio of chlorine to HFC-245fa at a suitable level, until most of the HFC-245fa is consumed. Additional HFC-245fa can be added to maintain the ratio of reactants at the desired level, as described above. Such a process can also be considered to be a titration-type process, since the titrating agent, chlorine, is added to HFC-245fa in a substantially continuous manner until the desired end-point is reached, e.g., until the HFC-245fa is sufficiently consumed that the reaction is terminated. Suitable analytical monitoring means, e.g., gas chromatography, can be employed to ascertain the concentrations of HFC-245fa and/or HCFC-235fa so as to avoid an excessively high ratio of chlorine to HFC-245fa.

Preferably the reaction is carried out in a substantially oxygen-free environment. This can be accomplished by, for example, flushing the reactor with an inert gas such as nitrogen, helium, argon, etc., prior to carrying out the reaction; nitrogen is preferred. It is expected that such an inert gas is itself substantially free of oxygen. Suitable commercial nitrogen is available that contains from about 100 ppm to about 2 wt. % oxygen and at levels in between including 0.1, 0.2, 0.5 and 1 wt. % oxygen. Nitrogen containing the lowest oxygen level commensurate with good economics should be used for the process. If nitrogen is used to flush the system, the nitrogen is preferably flushed from the reactor, e.g., with chlorine and/or HFC-245fa, before the reactants are introduced and the actinic radiation is activated. Alternatively, the use of nitrogen or an inert gas can be avoided and the reactor can be flushed with chlorine and/or HFC-245fa prior to carrying out the reaction. In any event, it is preferred that the reactor be substantially free of inert gas at the start of the reaction. In this context, substantially free means that the reactor contains less than about 10 weight % inert gas; more preferably less than about 5%; still more preferably less than about 3%; for example from less than about 1% to about 2%. In the preferred method of carrying out the process of the present invention, the reaction is carried out in the substantial absence of an inert gas such as nitrogen or helium; in other words, only the reactants and products of the reaction are present in the reaction zone except for the possible presence of trace levels of an inert gas diluent, e.g., less than about 1 wt. % of such a material.

The pressure in the reaction zone is not a critical variable for the process of the present invention. For example, the pressure can vary from slightly less than ambient pressure of one atmosphere (about 101 kPa) to a pressure somewhat greater than one atmosphere; generally the process can be carried out under pressures of from about one atmosphere up to about 3.5 atmospheres (about 354 kPa). Suitable account should be taken of the fact that the reactants, the desired product $CF_3CH_2CF_2Cl$, or HCFC-235fa, and by-product HCl can have significant vapor pressure. In particular, if the process is carried out in a closed system as a batch process, the changing amounts of reactants and reaction products should be taken into account to avoid excessive pressure build-up.

The source of irradiation for the photochlorination is not critical and it may be provided by any conventional source such as sun lamps, mercury vapor lamps (high, medium and low pressure types), bright incandescent and fluorescent lamps. Although any type of irradiation may be suitable, including visible light and ultraviolet light, ultraviolet light is preferred. The wavelength of the light can be from about 2000 to about 14500 Angstroms; for example from about 2500 to about 14000 Angstroms. The light source preferably radiates at from about 2700 Angstroms to about 5000 Angstroms; more preferably from about 2000 Angstroms to about 5000 Angstroms; most preferably from about 3000 Angstroms to about 4000 Angstroms. No advantage accrues from using radiation having wavelengths above about 5000 Angstroms.

As described above, the photochlorination reaction produces HCl in addition to the desired product. In one embodiment, following reaction or contact of the reactants in the presence of actinic radiation, the reactants and reaction products, including HCl, HCFC-235fa and possible multichlorinated products are contacted with an aqueous solution selected from the group consisting of a metal bisulfite, carbonate and hydroxide wherein the metal is selected from the group consisting of Group 1 and Group 2 according to the New Notation of the Periodic Table of the Elements. In particular, HCl can be removed from the product stream using conventional means such as absorption by a water or caustic scrubber, or distillation. The desired reaction product, HCFC-235fa can be separated from the overall reaction product stream or composition, which may include multichlorinated product, by using conventional means such as fractionation, distillation or liquid-liquid extraction. Unreacted HFC-245fa can be recycled back to the photochlorination reaction provided that it is treated to avoid undesirable impurities that may be present as a result of the separation processes, e.g., water. The effluent from the reactor also includes unreacted chlorine gas that can first be separated and purified by conventional methods and recycled.

All references herein to elements or metals belonging to a certain Group refer to the Periodic Table of the Elements as it appears in Hawley's Condensed Chemical Dictionary, 13$^{th}$ Edition. Also, any references to the Group or Groups shall be to the Group or Groups as reflected in this Periodic Table of Elements using the "New Notation" system for numbering groups.

The following examples are given as specific illustrations of the invention. It should be understood, however, that the invention is not limited to the specific details set forth in the examples. All parts and percentages in the examples, as well as in the remainder of the specification, are by weight unless otherwise specified.

Further, any range of numbers recited in the specification or paragraphs hereinafter describing or claiming various aspects of the invention, such as that representing a particular set of properties, units of measure, conditions, physical states or percentages, is intended to literally incorporate expressly herein by reference or otherwise, any number falling within such range, including any subset of numbers or ranges subsumed within any range so recited. The term "about" when used as a modifier for, or in conjunction with, a variable, is intended to convey that the numbers and ranges disclosed herein are flexible and that practice of the present invention by those skilled in the art using temperatures, concentrations, amounts, contents, carbon numbers, and properties that are outside of the range or different from a single value, will achieve the desired result, namely, photochlorination process for the preparation of chlorinated HFC-245fa, or HCFC-235fa.

EXAMPLES

The apparatus used for photochlorination in the following examples consisted of a 1 liter glass reactor equipped with: a condenser or cold trap (operating at about −78° C.); a magnetic stirrer for the reaction zone; a water cooled, quartz immersion well for placement of a 450 watt, quartz, medium pressure, mercury vapor lamp (providing radiation at about 200–400 nm); and an inlet for the introduction of chlorine and an outlet for gaseous products. The apparatus is available from Ace Glass Co., Vineland, N.J.

Gas chromatography, GC, conditions were as follows: initial temperature, 35° C., initial time, 2 min; ramp rate 15° C./min; final temperature, 250° C., final time 5 minutes; column brand, Supelco SPB-1, 30 m, 0.32 mm bore, 0.25 mm film. The products were further characterized by NMR and mass spectral analyses.

Example 1

Preparation of $CF_3CH_2CF_2Cl$ (HCFC-235fa)

The reactor described above was cooled and maintained at about 0° C. during the photochlorination reaction. Initially, the reactor was purged of air using nitrogen. Chlorine gas was then introduced to displace the nitrogen. Thereafter, 335 g (2.5 mol) of $CF_3CH_2CHF_2$ (HFC-245fa) was charged to the reactor. A total of 208 g (2.9 mol) of chlorine gas was bubbled into the $CF_3CH_2CHF_2$ over a period of about 24 hours while the reactants were being irradiated. At the end of the 24 hour period, GC analysis indicated a 96% conversion of HFC-245fa (retention time 1.9 min) to the desired product HCFC-235fa (retention time 2.1 min). The reaction mixture was washed with 100 mL of a cooled (about 2° C.) solution of aqueous sodium bisulfite (10 wt. %) and distilled (boiling point=26–28° C.) to afford 383 g $CF_3CH_2CF_2Cl$ (yield, 91%). Absent cooling of the wash solution, loss of product by vaporization has been observed due to a slight exotherm during the washing step. No multichlorinated products were detected.

Example 2

Reaction of HFC-245fa with Excess Chlorine

This experiment was conducted as described in Example 1 with the exception that excess chlorine was used such that the mole ratio of HFC-245fa to $Cl_2$ was 1:1.62. GC analysis of the product revealed that 7% of the HFC-245fa had been converted to a multichlorinated product, 1,1,1,3,3-pentafluoro-2,2,3-trichloropropane, $CF_3CCl_2CF_2Cl$, (retention time, 3.2 min) which was identified by mass spectral analysis.

Example 3

Reaction of HFC-245fa with Excess Chlorine

This experiment was conducted as described in Example 1 except that the mole ratio of HFC-245fa to chlorine was adjusted to be 1:1.3. Analysis of the product mixture by GC revealed that the multichlorinated product, $CF_3CCl_2CF_2Cl$ was present at a 2% concentration level. Examples 2 and 3 demonstrate that the HFC245fa/$Cl_2$ ratio should be closely controlled to avoid the formation of undesirable, multichlorinated by-products.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art, without departing from the spirit of the invention.

What is claimed is:

1. A process for preparing 1-chloro-1,1,3,3,3-pentafluoropropane, $CF_3CH_2CF_2Cl$, comprising contacting in a reaction zone in the substantial absence of oxygen, reactants comprising chlorine and 1,1,1,3,3-pentafluoropropane, $CF_3CH_2CHF_2$, and subjecting said reactants to actinic radiation, wherein: (A) inert gas is present at a concentration equal to or less than about 5 wt. % of the total weight of said reactants; and (B) the concentration of chlorinated product produced having greater than one chlorine present in the molecule is less than or equal to about 10 wt. %.

2. The process claim 1 wherein said inert gas is present at a concentration of less than 3 wt. %.

3. The process of claim 2 wherein said oxygen concentration present in said reaction zone is less than about 2 wt. %.

4. The process of claim 1 wherein said reactants are individually substantially in the liquid phase or the vapor phase.

5. The process of claim 4 wherein said $CF_3CH_2CHF_2$ is substantially in the liquid phase and said chlorine is dissolved in said liquid phase and is also present in the vapor phase.

6. The process of claim 4 wherein said $CF_3CH_2CHF_2$ is substantially saturated with said chlorine prior to subjecting said reactants to actinic radiation.

7. The process of claim 6 wherein said actinic radiation is provided by a light source selected from the group consisting of white light and ultraviolet light.

8. The process of claim 1 wherein the concentration of chlorinated product having greater than one chlorine present in the molecule is less than about 6 wt. %.

9. The process of claim 8 wherein the concentration of chlorinated product having greater than one chlorine present in the molecule is less than about 4 wt. %.

10. The process of claim 7 wherein said light source has a wavelength of from about 2,000 to about 14,500 Angstroms.

11. The process of claim 10 wherein said light source has a radiation maximum of from about 2,700 to about 5,000 Angstroms.

12. The process of claim 10 wherein said maximum is from about 2,000 to about 5,000 Agstroms.

13. The process of claim 1 conducted at a temperature of from about −5° C. to about +10° C.

14. The process of claim 13 wherein said temperature is from about 0° C. to about +2° C.

15. The process of claim 1 wherein following said contact, said reactants and any reaction products are contacted with an aqueous solution selected from the group consisting of a metal bisulfite, carbonate and hydroxide wherein said metal is selected from the group consisting of Group 1 and Group 2 according to the new notation of the periodic table of the elements.

16. The process of claim 15 wherein said aqueous solution is sodium bisulfite.

17. The process of claim 16 wherein said sodium bisulfite, prior to being brought into contact with said reactants and reaction products is cooled to a temperature of from about −0° C. to about +2° C.

18. The process of claim 1 wherein the molar ratio of chlorine to $CF_3CH_2CHF_2$ is from about 0.2:1 to about 1.5:1.

19. The process of claim 18 wherein said molar ratio of chlorine to $CF_3CH_2CHF_2$ is from about 0.5:1 to about 1.3:1.

20. The process of claim 19 wherein said molar ratio of chlorine to $CF_3CH_2CHF_2$ is from about 0.75:1 to about 1.25:1.

21. The process of claim 20 wherein the molar ratio of chlorine to $CF_3CH_2CHF_2$ is from about 0.9:1 to about 1.2:1.

22. The process of claim 18 wherein said molar ratio of chlorine to $CF_3CH_2CHF_2$ is from about 1.0:1 to about 1.3:1.

23. The process of claim 22 wherein said molar ratio of chlorine to $CF_3CH_2CHF_2$ is from about 1.0:1 to about 1.2:1.

24. Process of claim 1 conducted in a continuous manner.

25. Process of claim 1 conducted as a titration process.

26. Process of claim 1 conducted as a batch process.

27. The process of claim 17 wherein, following contact with said sodium bisulfite solution, said reactants and said reaction products are further subjected to at least one separation step in order to produce substantially pure $CF_3CH_2CF_2Cl$.

28. The process of claim 27 wherein said separation comprises fractionation.

29. The process of claim 27 wherein said separation comprises distillation.

30. A process for the preparation of substantially pure 1-chloro-1,1,3,3,3-pentafluoropropane, $CF_3CH_2CF_2Cl$, comprising:

(1) contacting in a reaction zone in the substantial absence of oxygen, at a temperature of from about −5° C. to about +10° C. reactants comprising chlorine and 1,1,1,3,3-pentafluoropropane, $CF_3CH_2CHF_2$, wherein said $CF_3CH_2CHF_2$ is substantially in the liquid phase and said chlorine is present in said liquid phase and is also present in the vapor phase; and (2) subjecting said reactants to actinic radiation wherein the source of said actinic radiation is a light source having a radiation spectrum of from about 2,000 to about 5,000 Angstroms; and wherein:

(A) said molar ratio of chlorine to $CF_3CH_2CHF_2$ is from about 0.2:1 to about 1.2:1;

(B) inert gas is present in said reaction zone at a concentration equal to or less than about 5 wt. % of the total weight of said reactants;

(C) the reactants and reaction products of step (1) are further subjected to contact with an aqueous solution of sodium bisulfite at a temperature of from about −5° C. to about +10° C.; and (D) the reactants and reaction products of step (B) are further subjected to at least one separation step selected from the group consisting of fractionation, distillation and liquid-liquid extraction.

* * * * *